United States Patent [19]  [11] 4,224,243
Aoyama et al.  [45] Sep. 23, 1980

[54] PROCESS FOR PRODUCING DIMETHYL FORMAMIDE

[75] Inventors: Tetsuo Aoyama; Shigeru Horie; Kozo Sano; Hidetaka Kiga; Kinichi Mizuno; Takeo Ikarashi, all of Niigata, Japan

[73] Assignee: Mitsubishi Gas Chemical Company, Inc., Tokyo, Japan

[21] Appl. No.: 49,604

[22] Filed: Jun. 18, 1979

[30] Foreign Application Priority Data

Jun. 23, 1978 [JP] Japan ................................ 53/76113

[51] Int. Cl.³ .................. C07C 102/00; C07C 103/36
[52] U.S. Cl. ................................................ 260/561 R
[58] Field of Search ..................................... 260/561 R

[56] References Cited
U.S. PATENT DOCUMENTS 2,677,706  5/1954  Giachino ......................... 260/561 R
3,446,842  5/1969  Nozaki ............................. 260/561 R
4,094,905  6/1978  Mizuno ........................... 260/561 R

FOREIGN PATENT DOCUMENTS 863800  12/1952  Fed. Rep. of Germany .
31-6510  4/1956  Japan .
718759  11/1954  United Kingdom .

*Primary Examiner*—Arthur P. Demers
*Attorney, Agent, or Firm*—Armstrong, Nikaido, Marmelstein & Kubovcik

[57] ABSTRACT

Dimethyl formamide with a high purity is produced in a high yield and a high selectivity by reaction of a mixture of monomethylamine and/or monomethyl formamide and trimethylamine, or the mixture further containing dimethylamine with carbon monoxide in the presence of metallic iron or an iron compound as a catalyst and hydrogen gas at a volumic rate of $H_2/CO$ of 0.05–3.

15 Claims, No Drawings

PROCESS FOR PRODUCING DIMETHYL FORMAMIDE

This invention relates to a process for producing dimethyl formamide (which will be hereinafter referred to as DMF) by reaction of a mixture of monomethylamine (which will be hereinafter referred to as MMA) and/or monomethyl formamide (which will be hereinafter referred to as MMF), and trimethylamine (which will be hereinafter referred to as TMA), or the mixture further containing dimethylamine (which will be hereinafter referred to as DMA) with carbon monoxide in the presence of metallic iron or an iron compound as a catalyst, which comprises conducting the reaction in the presence of a hydrogen gas at the same time.

Generally, DMF has been so far produced by reaction of DMA with carbon monoxide or methyl formate. DMA used therein is usually produced by dehydration reaction of methyl alcohol and ammonia but a large amount of MMA and TMA are produced as by-products at the same time in addition to DMA. However, MMA and TMA have a smaller industrial demand than that for DMA, and thus most of these two kinds of amines are usually recycled to the methylamine synthesis system to conduct a disproportionation reaction to DMA. In view of these facts, the present inventors made extensive studies of a process for synthesizing DMF from MMA and TMA as starting materials, and, as a result, have found a novel process for producing DMF from MMF readily obtainable from MMA and carbon monoxide, TMA, and carbon monoxide (U.S. Pat. No. 4,094,905) and a process for producing DMF from MMA, TMA and carbon monoxide or from MMA, DMA, TMA and carbon monoxide using metallic iron or an iron compound as a catalyst (U.S. patent application Ser. No. 917,894; British patent application No. 27465/78; DOS No. 2827633).

As a result of further studies, the present inventors have found that presence of an appropriate amount of hydrogen in a feedstock gas even in any of said three processes using the metallic iron or iron compound as the catalyst can elevate a selectivity to DMF and a DMF yield, and also has a good effect even upon the quality of product DMF obtained by distillation of the product solution.

It is a surprising fact that hydrogen, when contained in the feedstock gas, has a good effect upon the reaction to form DMF, and furthermore a gas mixture of carbon monoxide and hydrogen obtained by partial oxidation or steam reforming of naphtha, methane, etc., a blast furnace gas from a steel plant can be directly utilized in the present invention. This is a great economical advantage, and thus the present invention has a great industrial significance.

Recently, DMF is widely utilized as a solvent in the production of polyurethane for artificial and synthetic leather and in the spinning of acylic or polyurethane synthetic fibers, or as an extracting agent for butadiene, isoprene, etc., where a considerably high quality is required for DMF. However, DMF separated by distillation from a product solution resulting from said reaction using pure carbon monoxide containing no hydrogen as the feedstock gas in the presence of the metallic iron or iron compound as the catalyst contains a very small amount of unseparated alkaline impurities, which gives some problem to the quality of the product. Whenever the reaction is carried out, on the other hand, using a carbon monoxide feedstock gas containing hydrogen according to the present invention, these alkaline impurities are hydrized and decomposed during the reaction, and no alkaline impurities are remained at all in the product DMF. That is, the quality problem can be completely solved with a secondary effect in the present invention.

The catalyst used in the present invention is metallic iron or an iron compound, and the iron compound includes, for example, oxides, halide, hydroxides, sulfides, inorganic acid salts such as sulfate, carbonate, etc., and organic acid salts such as formate, acetate, oxalate, etc. of iron, and iron carbonyl compounds, such as iron pentacarbonyl, etc. It seems that metallic iron and other iron compounds than the carbonyl compounds are formed into complicated iron carbonyl compounds under the reaction conditions in the presence of carbon monoxide, and the resulting iron carbonyl compounds perform a catalytic action, but their form of action has not been clarified. The iron carbonyl compound perform a catalytic action not always in the given form, but possibly in the other form of iron carbonyl compound converted from the given form.

The catalyst is used in an amount of 0.01–300 mg-atom, preferably 0.1–300 mg-atom, more preferably 1–100 mg-atom as iron atom per mole of starting material amines and MMF. If the amount of the catalyst is less than the lower limit of said range, the yield is low, whereas the amount of the catalyst over the upper limit of said range is not objectionable, but uneconomical.

The reaction is carried out under a pressure of at least 10 kg/cm² gage, preferably 50–500 kg/cm² gage. If the pressure is below 10 kg/cm² gage, side reactions are unpreferably promoted, whereas the pressure over 500 kg/cm² gage is not objectionable from the viewpoint of reaction, but is not economically practical.

Hydrogen is mixed with carbon monoxide at a volumic ratio of $H_2/CO$ of 0.05–3, preferably 0.1–2. If hydrogen is mixed at a ratio over the upper limit of said range, the catalyst undergoes decomposition, whereas the effect of the present invention cannot be obtained at a ratio below the lower limit of said range. The gas mixture of carbon monoxide and hydrogen also plays a role of maintaining the reaction pressure, but so long as the amount of carbon monoxide is in excess of the theoretical one and the hydrogen is mixed therein at a ratio within said range, a gas further containing an inert gas such as nitrogen, methane, carbon dioxide, etc. can be used to maintain the reaction pressure.

Reaction is carried out at a temperature of 50°–350° C., preferably 100°–300° C. A satisfactory reaction rate cannot be obtained below 50° C., whereas decomposition of the product or decrease in DMF yield will be brought about above 350° C.

In the present invention, it seems that MMA and MMF undergo the reactions represented by the following formulae (1) and (2), together with TMA, respectively, whereas DMA alone undergoes the reaction represented by the following formula (3).

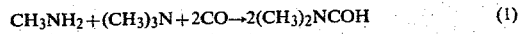

$$CH_3NH_2 + (CH_3)_3N + 2CO \rightarrow 2(CH_3)_2NCOH \quad (1)$$

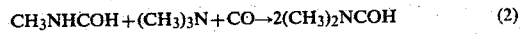

$$CH_3NHCOH + (CH_3)_3N + CO \rightarrow 2(CH_3)_2NCOH \quad (2)$$

$$(CH_3)_2NH + CO \rightarrow (CH_3)_2NCOH \quad (3)$$

Reaction formulae (1) and (2) show only relations between the starting materials and the product, and it seems that actually reactions represented by the following reactions (4), (5) and (6) take place, and DMA formed in the reactions (5) and (6) undergoes reaction (3).

$$CH_3NH_2 + CO \rightarrow CH_3NHCOH \quad (4)$$

$$CH_3NH_2 + (CH_3)_3N \rightarrow 2(CH_3)_2NH \quad (5)$$

$$CH_3NHCOH + (CH_3)_3N \rightarrow (CH_3)_2NCOH + (CH_3)_2NH \quad (6)$$

Molar ratio of TMA to MMA and/or MMF is 0.1–10, preferably 0.3–5. The amount of unreacted reactants is increased outside said range of the molar ratio, making the process impractical. On the other hand, there is no particular restriction to a molar ratio between DMA and other methylamines and/or MMF.

In the present invention, it is not essential to use a solvent, but use of a small amount of a solvent can facilitate a control of reaction temperature and also can increase a yield. The solvent includes amide solvents such as DMF, N-methylpyrolidone, etc.; saturated aliphatic hydrocarbons such as hexane, heptane, octane, etc.; aromatic hydrocarbon such as benzene, toluene, xylene, etc., and so on. When MMF is used as the starting material, MMF can act also as the solvent, and thus it is not necessary to add other solvent to the reaction system.

The present invention can be carried out batchwise or continuously.

According to the present invention, dimethyl formamide with a high purity can be produced in high yield and a high selectivity, using a gas mixture of carbon monoxide and hydrogen, which is cheap and readily available as a starting material gas, and MMA and TMA having a less demand among three kinds of amines formed from methanol and ammonia, and MMF readily obtainable from MMA and carbon monoxide as a whole or a portion of the starting materials, and thus the present invention has a very great industrial significance.

The present invention will be described in detail below, referring to Examples and Comparative Examples, where DMF yield and DMF selectivity are calculated according to the following formulae:

$$\text{DMF yield (\% by mole)} = \frac{\text{Moles of DMF obtained} \times 100}{\text{Moles of (total methylamines + MMF) charged}}$$

$$\text{DMF selectivity (\% by mole)} = \frac{\text{Moles of DMF obtained} \times 100}{\text{Moles of (total methylamines + MMF) charged} - \text{Moles of remaining (total methylamines + MMF)}}$$

The formulae should be calculated according to a combination of starting materials. For example, when no MMF is used as the starting material, calculation should be made, presuming that the moles of MMF charged is zero.

EXAMPLE 1

Into an autoclave (made of Hastelloy C) having a net capacity of 100 ml were charged 6.83 g of MMA, 10.14 g of TMA, 1.33 g of iron pentacarbonyl (Fe(CO)$_5$), and 5.9 g of N-methylpyrolidone. Reaction was carried out under a pressure of 200 kg/cm$^2$ gage attained by a gas mixture of carbon monoxide and hydrogen (CO:H$_2$=61.3:38.7 by volume) at 207° C. for 2 hours. The formed amides were analyzed by gas chromatography, and it was found that 13.03 g of DMF and 4.74 g of MMF were obtained, and these results corresponded to DMF yield of 45.5% and DMF selectivity of 91.3%.

EXAMPLE 2

Into the same autoclave as used in Example 1 were charged 6.51 g of MMA, 10.33 g of TMA, 1.27 g of iron pentacarbonyl and 6.0 g of N-methylpyrolidone. Reaction was carried out under a pressure of 280 kg/cm$^2$ gage attained by a gas mixture of carbon monoxide and hydrogen (CO:H$_2$=34.6:65.4 by volume) at 205° C. for two hours. 12.68 g of DMF and 4.43 g of MMF were obtained. DMF yield was 45.1%, and DMF selectivity was 89.7%.

COMPARATIVE EXAMPLE 1

In the same autoclave as used in Example 1 were charged 6.43 g of MMA, 10.32 g of TMA, 1.37 g of iron pentacarbonyl, and 6.0 g of N-methylpyrolidone. Reaction was carried out under a pressure of 200 kg/cm$^2$ gage attained by pure carbon monoxide at 208° C. for two hours. DMF yield was 31.4%, and DMF selectivity was 72.0%.

EXAMPLE 3

Into the same autoclave as used in Example 1 were charged 6.96 g of MMA, 9.58 g of TMA, 0.88 g of iron sulfate (FeSO$_4$), and 6.1 g of N-methylpyrolidone. Reaction was carried out under a pressure of 200 kg/cm$^2$ gage attained by a gas mixture of carbon monoxide and hydrogen (CO:H$_2$=84.2:15.8 by volume) at 208° C. for two hours. 14.02 g of DMF and 4.66 g of MMF were obtained. DMF yield was 49.6%, and DMF selectivity was 94.6%.

EXAMPLE 4

Into the same autoclave as used in Example 1 were charged 7.14 g of MMA, 9.76 g of TMA, 0.98 g of iron sulfate and 6.0 g of N-methylpyrolidone. Reaction was carried out under a pressure of 200 kg/cm$^2$ gage attained by a gas mixture of carbon monoxide and hydrogen (CO:H$_2$=76:24 by volume) at 207° C. for 2 hours. DMF yield was 45.7%, and DMF selectivity was 87.3%.

COMPARATIVE EXAMPLE 2

Into the same autoclave as used in Example 1 were charged 6.93 g of MMA, 9.62 g of TMA, 0.98 g of iron sulfate and 6.0 g of N-methylpyrolidone. Reaction was carried out under a pressure of 200 kg/cm$^2$ gage attained by pure carbon monoxide at 203° C. for two hours. DMF yield was 31.4%, and DMF selectivity was 63.7%.

EXAMPLE 5

Continuous reaction is carried out in a reactor tube (made of Hastelloy C, 30 mm in diameter×900 mm long) by supplying a feedstock solution containing 10.5% by weight of MMA, 16.3% by weight of DMA, 52.6% by weight of TMA, 16.7% by weight of MMF and 3.94% by weight of iron pentacarbonyl and a feedstock gas mixture of carbon monoxide and hydrogen (CO:H$_2$=62.7:37.3 by volume) to the lower part of the reactor tube under the following reaction conditions:

Reaction pressure: 200 kg/cm$^2$ gage
Reaction temperature: 238° C.
Apparent residence time of the solution: about 1.5 hours
Space velocity (SV): 200 hr$^{-1}$ Product solution under the stationary state was analyzed by gas chromatography. DMF yield was 41.2%, and DMF selectivity was 98.2%.

The product solution was collected, removed from unreacted amines, and then separated from the catalyst, and DMF was rectified in a packed column (50 mm in diameter × 1,700 mm high) in a reflux ratio of 5, and pH of the resulting DMF was 7.0-9.0.

COMPARATIVE EXAMPLE 3

Continuous reaction and rectification were carried out in the same manner as in Example 5, except that a feedstock solution containing 10.5% by weight of MMA, 15.6% by weight of DMA, 53.0% by weight of TMA, 17.3% by weight of MMF and 3.7% by weight of iron pentacarbonyl was used and pure carbon monoxide gas was used as a feed-stock gas in place of those used in Example 5. DMF yield was 32.0%, and DMF selectivity was 82.1%. The resulting DMF had a pH of 12-13.

EXAMPLE 6

Into an autoclave (made of Hastelloy C) having a net capacity of 100 ml were charged 10.63 g of MMF, 10.38 g of TMA, 1.29 g of iron pentacarbonyl, and 10.6 g of N-methylpyrolidone. Reaction was carried out under a pressure of 200 kg/cm² gage attained by a mixture of carbon monoxide and hydrogen ($CO:H_2=64.3:35.7$ by volume) at 237° C. for two hours. DMF yield was 58.1%, and DMF selectivity was 97.5%.

EXAMPLE 7

Into the same autoclave as used in Example 6 were charged 10.63 g of MMF, 10.33 g of TMA, 1.35 g of iron pentacarbonyl and 10.6 g of N-methylpyrolidone. Reaction was carried out under a pressure of 200 kg/cm² gage attained by a gas mixture of carbon monoxide and hydrogen ($CO:H_2=33.7:66.3$ by volume) at 236° C. for 2 hours. DMF yield was 43.3%, and DMF selectivity was 85.7%.

COMPARATIVE EXAMPLE 4

Into the same autoclave as used in Example 6 were charged 10.87 g of MMF, 10.16 g of TMA, 1.39 g of iron pentacarbonyl, and 10.9 g of N-methylpyrolidone. Reaction was carried out under a pressure of 200 kg/cm² gage attained by pure carbon monoxide at 236° C. for two hours. DMF yield was 39.0%, and DMF selectivity was 77.5%.

EXAMPLE 8

Into the same autoclave as used in Example 6 were charged 5.63 g of DMA, 8.35 g of TMA, 8.00 g of MMF, and 1.04 g of iron pentacarbonyl. Reaction was carried out under a pressure of 200 kg/cm² gage attained by a gas mixture of carbon monoxide and hydrogen ($CO:H_2=77.7:22.3$ by volume) at 235° C. for two hours. DMF yield was 63.4%, and DMF selectivity was 94.4%.

COMPARATIVE EXAMPLE 5

Into the same autoclave as used in Example 6 were charged 5.56 g of DMA, 8.28 g of TMA, 8.04 g of MMF and 1.08 g of iron pentacarbonyl. Reaction was carried out under a pressure of 200 kg/cm² gage attained by pure carbon monoxide at 235° C. for two hours. DMF yield was 46.9%, and DMF selectivity was 80.7%.

EXAMPLE 9

Into the same autoclave as used in Example 6 were charged 5.79 g of MMA, 12.53 g of TMA, 1.98 g of iron iodide ($FeI_2$), and 6.24 g of N-methylpyrolidone. Reaction was carried out under a pressure of 200 kg/cm² gage attained by a gas mixture of carbon monoxide and hydrogen ($CO:H_2=65:35$ by volume) at 210° C. for two hours. DMF yield was 48.8%, and DMF selectivity was 87.6%.

COMPARATIVE EXAMPLE 6

Into the same autoclave as used in Example 6 were charged 5.65 g of MMA, 12.79 g of TMA, 1.98 g of iron iodide, and 6.22 g of N-methylpyrolidone. Reaction was carried out under a pressure of 200 kg/cm² gage attained by pure carbon monoxide at 208° C. for two hours. DMF yield was 33.6%, and DMF selectivity was 73.4%.

EXAMPLE 10

Into an autoclave (made of SUS 304) having a net capacity of 300 ml were charged 13.21 g of MMA, 18.92 g of DMA, 23.47 g of TMA, 14.51 g of MMF and 4.03 g of iron formate ($Fe(HCOO)_3$). Reaction was carried out under a pressure of 230 kg/cm² gage attained by a gas mixture of carbon monoxide and hydrogen ($CO:H_2=18:82$ by volume) at 235° C. for 2 hours. The formed amide were analyzed by gas chromatography, and it was found that DMF yield and DMF selectivity were 57.8% and 97.3%, respectively. The resulting DMF rectified in the same manner as in Example 5 had a pH of 7.8.

EXAMPLE 11

Into the same autoclave as used in Example 6 were charged 7.15 g of MMA, 10.65 g of TMA, 1.10 g of iron hydroxide ($Fe(OH)_3$) and 6.0 g of N-methylpyrolidone. Reaction was carried out under a pressure of 200 kg/cm² gage attained by a gas mixture of carbon monoxide and hydrogen ($CO:H_2=22:78$ by volume) at 150° C. for 6 hours. DMF yield was 42.2%, and DMF selectivity was 96.3%.

EXAMPLE 12

Into the same autoclave as used in Example 6 were charged 6.94 g of MMA, 10.35 g of TMA, 0.16 g of iron oxide ($Fe_2O_3$) and 6.0 g of N-methylpyrolidone. Reaction was carried out under a pressure of 250 kg/cm² gage attained by a gas mixture of carbon monoxide and hydrogen ($CO:H_2=27:73$ by volume) at 230° C. for 4 hours. DMF yield was 46.8% and DMF selectivity was 93.8%.

What is claimed is:

1. A process for producing dimethyl formamide by reaction of a mixture selected from the group consisting of the mixtures of: (a) monomethyl amine and trimethyl amine, (b) monomethyl amine, monomethyl formamide and trimethyl amine, (c) monomethyl formamide and trimethyl amine, (d) monomethyl amine, trimethyl amine and dimethyl amine, (e) monomethyl amine, monomethyl formamide, trimethyl amine and dimethyl amine and (f) monomethyl formamide, trimethyl amine and dimethyl amine; with carbon monoxide, said process carried out in the presence of a compound selected from the group consisting of metallic iron and an iron compound as a catalyst, wherein said process comprises conducting the reaction in the presence of hydrogen gas.

2. A process according to claim 1, wherein a ratio of hydrogen to carbon monoxide by volume is 0.05–3.

3. A process according to claim 2, wherein the ratio of hydrogen to carbon monoxide by volume is 0.1–2.

4. A process according to claim 1, wherein the reaction is carried out at 50°–350° C.

5. A process according to claim 1, wherein the reaction is carried out at 100°–300° C.

6. A process according to claim 1, wherein a molar ratio of trimethylamine to monomethylamine and/or monomethyl formamide is 0.1–10.

7. A process according to claim 6, wherein the molar ratio of trimethylamine to monomethylamine and/or monomethyl formamide is 0.3–5.

8. A process according to claim 1, wherein the iron compound is an oxide, a halide, a hydroxide, a sulfide, a sulfate, a carbonate, a formate, an acetate and an oxalate of iron, or an iron carbonyl.

9. A process according to claim 1, wherein the catalyst is used in an amount of 0.01–300 mg-atom as iron atom per mole of the amines and monomethyl formamide.

10. A process according to claim 9, wherein the catalyst is used in an amount of 0.1–300 mg-atom as an iron atom per mole of the amines and monomethyl formamide.

11. A process according to claim 10, wherein the catalyst is used in an amount of 1–100 mg-atom as an iron atom per mole of the amines and monomethyl formamide.

12. A process according to claim 1, wherein the reaction is carried out in the presence of a solvent.

13. A process according to claim 12, wherein the solvent is dimethyl formamide, N-methylpyrolidone, hexane, heptane, octane, benzene, toluene or xylene.

14. A process according to claim 1, wherein the reaction is carried out batch-wise.

15. A process according to claim 1, wherein the reaction is carried out continuously.